US009056821B2

(12) United States Patent
Hasyagar et al.

(10) Patent No.: US 9,056,821 B2
(45) Date of Patent: *Jun. 16, 2015

(54) PROMOTER CATALYST SYSTEM WITH SOLVENT PURIFICATION

(71) Applicant: SABIC Global Technologies B.V., Bergen op Zoom (NL)

(72) Inventors: Umesh Krishna Hasyagar, Karnataka (IN); Rathinam Jothi Mahalingam, Karnataka (IN); Kishan Gurram, Karnataka (IN); Paul Eijsbouts, Nieuwkuijk (NL)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/249,875

(22) Filed: Apr. 10, 2014

(65) Prior Publication Data
US 2014/0221697 A1 Aug. 7, 2014

Related U.S. Application Data

(63) Continuation of application No. 13/099,026, filed on May 2, 2011, now Pat. No. 8,735,634.

(51) Int. Cl.
C07C 37/20 (2006.01)
C07C 37/84 (2006.01)

(52) U.S. Cl.
CPC .............. C07C 37/20 (2013.01); C07C 37/84 (2013.01)

(58) Field of Classification Search
None
See application file for complete search history.

(56) References Cited

U.S. PATENT DOCUMENTS

| 3,049,568 | A | 8/1962 | Apel et al. |
| 3,394,089 | A | 7/1968 | McNutt et al. |
| 3,673,262 | A | 6/1972 | Prahl et al. |
| 4,045,379 | A | 8/1977 | Kwantes et al. |
| 4,052,466 | A | 10/1977 | Sun |
| 4,191,843 | A | 3/1980 | Kwantes et al. |
| 4,294,995 | A | 10/1981 | Faler et al. |
| 4,308,404 | A | 12/1981 | Kwantes et al. |
| 4,308,405 | A | 12/1981 | Kwantes |
| 4,346,247 | A | 8/1982 | Faler et al. |
| 4,365,099 | A | 12/1982 | Faler et al. |
| 4,391,997 | A | 7/1983 | Mendiratta |
| 4,396,728 | A | 8/1983 | Faler |
| 4,400,555 | A | 8/1983 | Mendiratta |
| 4,423,252 | A | 12/1983 | Maki et al. |
| 4,424,283 | A | 1/1984 | Faler et al. |
| 4,455,409 | A | 6/1984 | Faler et al. |
| 4,478,956 | A | 10/1984 | Maki et al. |
| 4,584,416 | A | 4/1986 | Pressman et al. |
| 4,590,303 | A | 5/1986 | Mendiratta |
| 4,595,704 | A | 6/1986 | Fazio |
| 4,820,740 | A | 4/1989 | Li |
| 4,822,923 | A | 4/1989 | Li |
| 4,825,010 | A | 4/1989 | Li |
| 4,859,803 | A | 8/1989 | Shaw |
| 4,918,245 | A | 4/1990 | Iimuro et al. |
| 5,015,784 | A | 5/1991 | Rudolph et al. |
| 5,087,767 | A | 2/1992 | Okamoto et al. |
| 5,212,206 | A | 5/1993 | Rudolph et al. |
| 5,233,096 | A | 8/1993 | Lundquist |
| 5,284,981 | A | 2/1994 | Rudolph et al. |
| 5,302,774 | A | 4/1994 | Berg et al. |
| 5,395,857 | A | 3/1995 | Berg et al. |
| 5,414,151 | A | 5/1995 | Pressman et al. |
| 5,414,152 | A | 5/1995 | Cipullo |
| 5,455,282 | A | 10/1995 | Berg et al. |
| 5,463,140 | A | 10/1995 | Wehmeyer et al. |
| 5,475,154 | A | 12/1995 | Lundquist et al. |
| 5,589,517 | A | 12/1996 | Sugawara et al. |
| 5,631,338 | A | 5/1997 | Inoue et al. |
| 5,698,600 | A | 12/1997 | Wulff et al. |
| 5,780,690 | A | 7/1998 | Berg et al. |
| 5,783,733 | A | 7/1998 | Kissinger |
| 5,914,431 | A | 6/1999 | Fennhoff |
| 6,133,190 | A | 10/2000 | Wehmeyer et al. |
| 6,211,417 | B1 | 4/2001 | Fengler et al. |
| 6,329,556 | B1 | 12/2001 | Sakura et al. |
| 6,414,199 | B1 | 7/2002 | Saruwatari |
| 6,429,343 | B1 | 8/2002 | Iwahara |
| 6,486,222 | B2 | 11/2002 | Kissinger et al. |
| 6,586,637 | B2 | 7/2003 | Iwahara |
| 6,653,513 | B1 | 11/2003 | Iwahara |
| 6,710,211 | B1 | 3/2004 | Heydenreich et al. |
| 6,727,394 | B2 | 4/2004 | Saruwatari |
| 6,730,816 | B2 | 5/2004 | Lundquist |

(Continued)

FOREIGN PATENT DOCUMENTS

| EP | 0313165 | 4/1989 |
| EP | 0620041 | 10/1994 |
| EP | 0676237 | 10/1995 |
| EP | 0693470 | 1/1996 |
| EP | 0770589 | 5/1997 |
| EP | 0788839 | 8/1997 |
| EP | 1160229 | 12/2001 |
| EP | 1201303 | 5/2002 |
| EP | 1222960 | 7/2002 |
| EP | 1273563 | 1/2003 |
| EP | 1371623 | 12/2003 |

(Continued)

OTHER PUBLICATIONS

Brunelle, "Polycarbonates," Encyclopedia of Polymer Science And Technology, Jan. 1, 2006, 1-33.

(Continued)

Primary Examiner — Brian J Davis
(74) Attorney, Agent, or Firm — Baker & Hostetler LLP

(57) ABSTRACT

Methods for performing a condensation reaction are disclosed. Specifically, various methods for the production of highly-pure bisphenol-A are disclosed in which an attached promoter ion exchange resin catalyst system is combined with a solvent crystallization step.

35 Claims, No Drawings

(56) References Cited

U.S. PATENT DOCUMENTS

| | | | |
|---|---|---|---|
| 6,740,784 | B2 | 5/2004 | Iwahara et al. |
| 6,825,386 | B2 | 11/2004 | Iwahara et al. |
| 7,112,702 | B2 | 9/2006 | Carvill et al. |
| 7,112,703 | B2 | 9/2006 | Neumann et al. |
| 7,129,382 | B2 | 10/2006 | Iwahara et al. |
| 8,735,634 | B2 * | 5/2014 | Hasyagar et al. ............. 568/728 |
| 2004/0116751 | A1 | 6/2004 | Carvill et al. |
| 2004/0181100 | A1 | 9/2004 | Lundquist |
| 2005/0070615 | A1 | 3/2005 | Terajima et al. |

FOREIGN PATENT DOCUMENTS

| | | |
|---|---|---|
| EP | 1232134 | 9/2004 |
| EP | 1459805 | 9/2004 |
| EP | 1520617 | 4/2005 |
| FR | 2685221 | 6/1993 |
| FR | 2685323 | 6/1993 |
| JP | 05271132 | 10/1993 |
| JP | 05294875 | 11/1993 |
| JP | 05294876 | 11/1993 |
| JP | 08/038910 | 2/1996 |
| JP | 08/071433 | 3/1996 |
| JP | 08/319248 | 12/1996 |
| JP | 08/325185 | 12/1996 |
| JP | 10/211434 | 8/1998 |
| JP | 10/251180 | 9/1998 |
| JP | 10/314595 | 12/1998 |
| JP | 10/328573 | 12/1998 |
| JP | 11/179210 | 7/1999 |
| JP | 11/246458 | 9/1999 |
| JP | 11/255748 | 9/1999 |
| JP | 2000/281607 | 10/2000 |
| JP | 2000/281608 | 10/2000 |
| JP | 2000/319216 | 11/2000 |
| JP | 2001/233812 | 8/2001 |
| WO | WO 97/08122 | 3/1997 |
| WO | WO 00/23408 | 4/2000 |
| WO | WO 00/50372 | 8/2000 |
| WO | WO 01/49640 | 7/2001 |
| WO | WO 01/53238 | 7/2001 |
| WO | WO 2006/083602 | 8/2006 |
| WO | WO 2008/100165 | 8/2008 |

OTHER PUBLICATIONS

FDA News & Events, Public Health Focus [online], Bisphenol A (BPA): Use in Food Contact Application, Update on Bisphenol A (BPA) for Use in Food Contact Applications, Jan. 2010, Updated Mar. 30, 2012 [retrieved on Mar. 16, 2013 from the Internet at URL: http://www.fda.gov/newsevents/publichealthfocus/ucm064437.htm], 6 pages.

"Polycarbonate Preparation with a Low Yellowness Index," Research Disclosure, Mason Publications, Hampshire, 2001, 449(49), 1-3.

* cited by examiner

PROMOTER CATALYST SYSTEM WITH SOLVENT PURIFICATION

CROSS REFERENCE TO RELATED PATENT APPLICATION

This application is a continuation of and claims priority to co-pending U.S. patent application Ser. No. 13/099,026 filed May 2, 2011, the disclosure of which is herein incorporated by reference in its entirety.

TECHNICAL FIELD

The present disclosure relates to catalyst systems, and specifically to promoter ion exchange resin catalyst systems.

TECHNICAL BACKGROUND

Many conventional condensation reactions utilize inorganic acid catalysts, such as sulfuric acid or hydrochloric acid. Use of such inorganic acid catalysts can result in the formation of undesirable byproducts that must be separated from the reaction stream. Ion exchange resin catalyst systems can also be used, but the inherent low acid concentration can require the use of a promoter or rate accelerator.

When used as part of the catalyst system, reaction promoters can improve reaction rate and selectivity. In the case of the condensation of phenol and ketone to form bisphenol-A (BPA), reaction promoters can improve selectivity for the desired para-para BPA isomer.

Reaction promoters can be used as bulk promoters, where the promoter is present as an unattached molecule in the reaction medium, or as an attached promoter, where the promoter is attached to a sulphonic acidic portion of the catalyst system.

In the synthesis of BPA, the use of 3-mercaptopropionic acid (3-MPA) can produce a significant quantity of the less desirable o,p-BPA isomer, as opposed to the preferred p,p-BPA isomer.

While much effort has been applied to the development and use of bulk and attached promoter systems, a need still exists for a manufacturing process and promoter catalyst system that can provide high purity reaction products. Thus, there is a need to address these and other shortcomings associated with existing promoter catalyst systems. These needs and other needs are satisfied by the compositions and methods of the present disclosure.

SUMMARY

In accordance with the purpose(s) of the invention, as embodied and broadly described herein, this disclosure, in one aspect, relates to catalyst systems, and specifically to promoter ion exchange resin catalyst systems.

In one aspect, the present disclosure provides a process for a chemical condensation reaction, the process comprising contacting at least two chemical reagents with an attached promoter ion exchange resin catalyst system to produce an effluent, and then subjecting the effluent to a solvent crystallization step.

In a second aspect, the present disclosure provides a process comprising contacting at least two chemical reagents with an attached promoter ion exchange resin catalyst system to produce an effluent, and then subjecting the effluent to a solvent crystallization step, wherein the attached promoter ion exchange resin catalyst system comprises cross-linked, sulfonated ion exchange resin having sulfonic groups and a degree of cross-linking of from 1% to 4%.

In a third aspect, the present disclosure provides a process comprising contacting at least two chemical reagents with an attached promoter ion exchange resin catalyst system, wherein the attached promoter ion exchange resin catalyst system comprises a dimethyl thiazolidine promoter.

In a fourth aspect, the present disclosure provides a process comprising contacting at least two chemical reagents with an attached promoter ion exchange resin catalyst system, wherein the attached promoter ion exchange resin catalyst system comprises a promoter that is ionically bound to from about 18% to about 25% of sulfonic acid groups present on the ion exchange resin.

In a fifth aspect, the present disclosure provides a process wherein prior to a solvent crystallization step, a reactor effluent is subjected to at least one of a separate ion exchange resin bed, a water removal step, a phenol recovery step, or a combination thereof.

In a sixth aspect, the present disclosure provides a bisphenol A reaction product having no or substantially no inorganic and/or sulfur impurities.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited.
Definitions Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a ketone" includes mixtures of two or more ketones.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not. For example, the phrase "optionally substituted alkyl" means that the alkyl group can or can not be substituted and that the description includes both substituted and unsubstituted alkyl groups.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

References in the specification and concluding claims to parts by weight of a particular element or component in a composition or article denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkoxy" as used herein is an alkyl group bound through a single, terminal ether linkage; that is, an "alkoxy" group may be defined as -OR where R is alkyl as defined above. A "lower alkoxy" group is an alkoxy group containing from one to six carbon atoms.

The term "alkenyl group" as used herein is a hydrocarbon group of from 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described above.

The term "carboxylic acid" as used herein is represented by the formula —C(O)OH.

The term "aldehyde" as used herein is represented by the formula —C(O)H.

The term "keto group" as used herein is represented by the formula —C(O)R, where R is an alkyl, alkenyl, alkynyl, aryl, aralkyl, cycloalkyl, halogenated alkyl, or heterocycloalkyl group described above.

The term "carbonyl group" as used herein is represented by the formula C=O.

The term "ether" as used herein is represented by the formula AOA$^1$, where A and A$^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "sulfo-oxo group" as used herein is represented by the formulas —S(O)$_2$R, —OS(O)$_2$R, or, —OS(O)$_2$OR, where R can be hydrogen, an alkyl, alkenyl, alkynyl, aryl, aralkyl, cycloalkyl, halogenated alkyl, or heterocycloalkyl group described above.

As used herein, the term "promoter catalyst system" is intended to refer to a catalyst system comprising a promoter, unless specifically stated to the contrary. A promoter catalyst system can also be referred to as a promoted catalyst system, indicating the presence of a promoter in the catalyst system.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

As briefly described above, the present disclosure provides a manufacturing process and a promoter catalyst system that can be useful in condensation reactions, such as, for example, the synthesis of bisphenol-A. Conventional ion exchange resin based BPA manufacturing processes utilize sulfur containing bulk promoters, such as 3-mercaptopropionic acid (3-MPA), that can degrade and generate undesirable sulfur compounds in the final product. These compounds can limit or prevent the use of BPA in demanding applications, such as food contact grade polycarbonate.

In one aspect, the present disclosure provides a manufacturing process that can produce high purity BPA, with no or substantially no inorganic, sulfur, or thermally degraded components. In another aspect, the present disclosure provides a manufacturing process that does not utilize a bulk promoter, such as, for example, 3-MPA. In yet another aspect, the present disclosure provides a manufacturing process and catalyst system that can provide high purity BPA, suitable for use in food contact polycarbonate applications. In still another aspect, the present disclosure provides a manufacturing process that comprises an attached promoter catalyst in combination with solvent crystallization.

Promoter systems can also be attached, wherein the promoter is attached to the catalyst system, such as the ion exchange resin. An exemplary attached promoter system utilizes a pyridyl ethylmercapton (PEM) promoter.

In one aspect, the methods described here can be useful for the preparation of BPA. It should also be noted that reactants for bisphenol condensation reactions can comprise phenols, ketones and/or aldehydes, or mixtures thereof. In one aspect, any specific recitation of a ketone, such as acetone, or an aldehyde, is intended to include aspects where only the recited species is used, aspects wherein the other species (e.g., aldehyde for ketone) is used, and aspects wherein a combination of species is used. In other aspects, the methods described herein can be useful for the preparation of other chemical species from, for example, condensation reactions.

In one aspect, phenol reactants can comprise an aromatic hydroxy compound having at least one unsubstituted position, and optionally one or more inert substituents such as hydrocarbyl or halogen at one or more ring positions. In one aspect, an inert substituent is a substituent which does not interfere undesirably with the condensation of the phenol and ketone or aldehyde and which is not, itself, catalytic. In another aspect, phenol reactants are unsubstituted in the position para to the hydroxyl group. As recited here, hydrocarbyl functionalities comprise carbon and hydrogen atoms, such as, for example, alkylene, alkyl, cycloaliphatic, aryl, arylene, alkylarylene, arylalkylene, alkylcycloaliphatic and alkylenecycloaliphatic are hydrocarbyl functions, that is, functions containing carbon and hydrogen atoms.

In one aspect, an alkyl group, if present in a phenol species, comprises from 1 to about 20 carbon atoms, or from 1 to about 5 carbon atoms, or from 1 to about 3 carbon atoms, such as, for example, various methyl, ethyl, propyl, butyl and pentyl isomers. In one aspect, alkyl, aryl, alkaryl and aralkyl substituents are suitable hydrocarbyl substituents on the phenol reactant.

In one aspect, other inert phenol substituents can include, but are not limited to alkoxy, aryloxy or alkaryloxy, wherein alkoxy includes methoxy, ethoxy, propyloxy, butoxy, pentoxy, hexoxy, heptoxy, octyloxy, nonyloxy, decyloxy and polyoxyethylene, as well as higher homologues; aryloxy, phenoxy, biphenoxy, naphthyloxy, etc. and alkaryloxy includes alkyl, alkenyl and alkylnyl-substituted phenolics. Additional inert phenol substituents can include halo, such as bromo, chloro or iodo.

While not intending to be limiting, exemplary phenols can comprise, phenol, 2-cresol, 3-cresol, 4-cresol, 2-chlorophenol, 3-chlorophenol, 4-chlorophenol, 2-tert-butylphenol, 2,4-dimethylphenol, 2-ethyl-6-methylphenol, 2-bromophenol, 2-fluorophenol, 2-phenoxyphenol, 3-methoxyphenol, 2,3,6-trimethylphenol, 2,3,5,6-tetramethylphenol, 2,6-xylenol, 2,6-dichlorophenol, 3,5-diethylphenol, 2-benzylphenol, 2,6-di-tertbutylphenol, 2-phenylphenol, 1-naphthol, 2-naphthol, and/or combinations thereof. In another aspect, phenol reactants can comprise phenol, 2- or 3-cresol, 2,6-dimethylphenol, resorcinol, naphthols, and/or combinations or mixtures thereof. In one aspect, a phenol is unsubstituted.

In one aspect, the phenol starting materials can be commercial grade or better. As readily understood by one of ordinary skill in the art commercial grade reagents may contain measurable levels of typical impurities such as acetone, alpha-methylstyrene, acetophenone, alkyl benzenes, cumene, cresols, water, hydroxyacetone, methyl benzofuran, methyl cyclopentenone, and mesityl oxide, among others.

In one aspect, ketones, if used, can comprise any ketone having a single carbonyl (C=O) group or several carbonyl groups, and which are reactive under the conditions used. In another aspect, ketones can be substituted with substituents that are inert under the conditions used, such as, for example those inert substituents recited above with respect to phenols.

In one aspect, a ketone can comprise aliphatic, aromatic, alicyclic or mixed aromatic-aliphatic ketones, diketones or polyketones, of which acetone, methyl ethyl ketone, diethyl ketone, benzyl, acetyl acetone, methyl isopropyl ketone, methyl isobutyl ketone, acetophenone, ethyl phenyl ketone, cyclohexanone, cyclopentanone, benzophenone, fluorenone, indanone, 3,3,5-trimethylcyclohexanone, anthraquinone, 4-hydroxyacetophenone, acenaphthenequinone, quinone, benzoylacetone and diacetyl are representative examples. In another aspect, a ketone having halo, nitrile or nitro substituents can also be used, for example, 1,3-dichloroacetone or hexafluoroacetone.

Exemplary aliphatic ketones can comprise acetone, ethyl methyl ketone, isobutyl methyl ketone, 1,3-dichloroacetone, hexafluoroacetone, or combinations thereof. In one aspect, the ketone is acetone, which can condense with phenol to produce 2,2-bis-(4-hydroxyphenyl)-propane, commonly known as bisphenol A. In another aspect, a ketone comprises hexafluoroacetone, which can react with two moles of phenol to produce 2,2-bis-(4-hydroxyphenyl)-hexafluoropropane (bisphenol AF). In another aspect, a ketone can comprise a ketone having at least one hydrocarbyl group containing an aryl group, for example, a phenyl, tolyl, naphthyl, xylyl or 4-hydroxyphenyl group.

Other exemplary ketones can include 9-fluorenone, cyclohexanone, 3,3,5-trimethylcyclohexanone, indanone, indenone, anthraquinone, or combinations thereof. Still other exemplary ketones can include benzophenone, acetophenone, 4-hydroxyacetophenone, 4,4'-dihydroxybenzophenone, or combinations thereof.

In one aspect, a ketone reactant can be commercial grade or better. As readily understood by one of ordinary skill in the art commercial grade reagents may contain measurable levels of typical impurities such as aldehydes, acetophenone, benzene, cumene, diacetone alcohol, water, mesityl oxide, and methanol, among others. In one aspect, a ketone, such as, for example, acetone, has less than about 250 ppm of methanol. In another aspect, the inventive catalyst systems of the present invention can tolerate higher concentrations of impurities, such that a ketone can comprise more than 250 ppm of methanol.

In other aspects, the various methods and catalyst systems described herein can be used for the condensation of phenols with aldehydes, for example, with formaldehyde, acetaldehyde, propionaldehyde, butyraldehyde or higher homologues of the formula RCHO, wherein R is alkyl of, for example, 1 to 20 carbon atoms. In one aspect, the condensation of two moles of phenol with one mole of formaldehyde produces bis-(4-hydroxyphenyl)methane, also known as Bisphenol F. It should also be understood that dialdehydes and ketoaldehydes, for example, glyoxal, phenylglyoxal or pyruvic aldehyde, can optionally be used.

Promoter Catalyst System—Ion Exchange Resin

The promoter catalyst system of the present disclosure comprises an ion exchange resin catalyst and a promoter. In one aspect, the ion exchange resin can comprise any ion exchange resin suitable for use in the catalyst system of the present invention. In another aspect, the ion exchange resin comprises a cross-linked cationic exchange resin. In another aspect, the ion exchange resin comprises a cross-linked sulfonated ion exchange resin having a plurality of sulfonic acid sites. In yet another aspect, the ion exchange resin is acidic or strongly acidic. In one aspect, at least a portion of the ion exchange resin comprises sodium polystyrene sulfonate. In still other aspects, the ion exchange resin can comprise a monodispersed resin, a polydispersed resin, or a combination thereof.

The specific chemistry of an ion exchange resin or any one or more polymer materials that form a part of an ion exchange resin can vary, and one of skill in the art, in possession of this disclosure, could readily select an appropriate ion exchange resin. In one aspect, the ion exchange resin comprises polystyrene or a derivatized polystyrene. In another aspect, the ion exchange resin comprises a polysiloxane or derivatized polysiloxane. It should also be understood that the catalyst system can, in one aspect, comprise multiple ion exchange resins of the same or varying composition, acidity, and/or degree of cross-linking.

In one aspect, the ion exchange resin can be cross-linked with the same or a different polymer material. In various aspects, the degree of cross-linking is from about 1 percent to about 8 percent, for example, about 1, 2, 3, 4, 5, 6, 7, 8, percent; from about 1 percent to about 4 percent, for example, about 1, 1.2, 1.4, 1.6, 1.8, 2, 2.2, 2.4, 2.6, 2.8, 3, 3.2, 3.4, 3.6, 3.8, or 4 percent; or from about 1.5 percent to about 2.5 percent, for example, about 1.5, 1.6, 1.7, 1.8, 1.9, 2, 2.1, 2.2, 2.3, 2.4, or 2.5 percent. In other aspects, the degree of cross-linking can be less than 1 percent or greater than 8 percent, and the present invention is not intended to be limited to any particular degree of cross-linking recited here. In a specific aspect, the degree of cross-linking is about 2 percent. In another aspect, the ion exchange resin is not cross-linked. While not wishing to be bound by theory, cross-linking of an ion exchange resin is not necessary, but can provide additional stability to the resin and the resulting catalyst system.

In one aspect, the ion exchange resin can be cross-linked using any conventional cross-linking agents, such as, for example, polycyclic aromatic divinyl monomers, divinyl benzene, divinyl toluene, divinyl biphenyl monomers, or combinations thereof.

In other aspects, the ion exchange resin comprises a plurality of acid sites, and has, before modification, at least about 3, at least about 3.5, at least about 4, at least about 5, or more acid milliequivalents per gram (meq/g) when dry. In a specific aspect, the ion exchange resin, before modification, has at least about 3.5 acid milliquivalents per gram when dry. In various aspects, any of the plurality of acid sites on an ion exchange resin can comprise a sulfonic acid functionality, which upon deprotonation produces a sulfonate anion functionality, a phosphonic acid functionality, which upon deprotonation produces a phosphonate anion functionality, or a carboxylic acid functionality, which upon deprotonation produces a carboxylate anion functionality.

Exemplary ion exchange resins can include, but are not limited to, DIAION® SK104, DIAION® SK1B, DIAION® PK208, DIAION® PK212 and DIAION® PK216 (manufactured by Mitsubishi Chemical Industries, Limited), A-121, A-232, and A-131, (manufactured by Rohm & Haas), T-38, T-66 and T-3825 (manufactured by Thermax), LEWATIT® K1131, LEWATIT® K1221 (manufactured by Lanxess), DOWEX® 50W2X, DOWEX® 50W4X, DOWEX® 50W8X resins (manufactured by Dow Chemical), Indion 180, Indion 225 (manufactured by Ion Exchange India Limited), and PUROLITE® CT-222 and PUROLITE® CT-122 (manufactured by Purolite).

Promoter Catalyst System—Promoter

The promoter of the attached promoter catalyst system of the present invention can comprise any promoter species suitable for use in the various methods described herein, and that can provide a desired high-purity product.

In one aspect, the promoter of the present invention can comprise pyridyl ethylmercapton (PEM). In another aspect, the promoter of the present invention can comprise dimethyl thiazolidine (DMT). In other aspects, the promoter of the present invention can comprise derivatives and/or analogues of pyridyl ethylmercapton, dimethyl thiazolidine, or a combination thereof. In another aspect the promoter of the present invention can comprise other promoter species not specifically recited herein. In another aspect, the promoter of the present invention can be represented by the formula below:

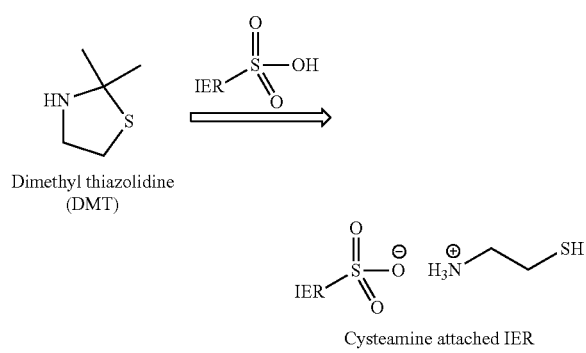

Dimethyl thiazolidine (DMT)

Cysteamine attached IER wherein the dimethyl thiazolidine is combined with an ion exchange resin so as to provide a cysteamine attached ion exchange resin.

In one aspect, the promoter can be contacted with the ion exchange resin so as to neutralize at least a portion of the available acid sites on the ion exchange resin, and attach thereto. In various aspects, the ion exchange resin is modified by neutralizing from about 10% to about 40% of the available acid sites with the promoter; or from about 18% to about 25% of the available acid sites with the promoter. In another aspect, the promoter is bound to from about 18% to about 25%, for example, about 18, 19, 20, 21, 22, 23, 24, or 25% of the acid sites on the ion exchange resin. In another aspect, the promoter is bound to from about 20% to about 24% of the acid sites on the ion exchange resin. In still another aspect, the promoter is bound to about 22% of the acid sites of the ion exchange resin.

In an exemplary process, the promoter is combined with a solvent to form a mixture. The mixture may further comprise an acid to improve solubility of the promoter. In one aspect, the amount of acid can be sufficient to solubilize the promoter but not enough to impede modification of the ion exchange resin. In one aspect, the amount of acid is typically less than or equal to about 1 equivalent; or less than or equal to about 0.25 equivalents, based on the number of moles of the promoter. Exemplary acids include, but are not limited to, hydrochloric acid (HCl), p-toluenesulfonic acid, trifluorocacetic acid, and acetic acid. In such an aspect, the mixture can be contacted with the ion exchange resin resulting in an ionic linkage between the promoter cation and anion (deprotonated acid site) of the ion exchange resin. Formation of the ionic linkage neutralizes the acid site.

The degree of neutralization may be determined in a number of ways. In one aspect, the modified ion exchange resin catalyst can be titrated to determine the amount of remaining acid sites.

Following modification (neutralization), the modified ion exchange resin catalyst can optionally be rinsed with a continuous flow of phenol to remove any remaining amounts of solvent from the modification. Alternatively, if acid was used to improve the solubility of the promoter, the modified ion exchange resin can optionally be rinsed with deionized water prior to rinsing with phenol. In one aspect, removing substantially all of the water is herein defined as removing greater than or equal to about 75%, greater than or equal to about 80%, or greater than or equal to about 85%, based on the total amount of water initially employed.

In one aspect, at least a portion of the promoter is ionically bound to the available acid sites of the ion exchange resin. In another aspect, all or substantially all of the promoter is ionically bound to acid sites of the ion exchange resin. In another aspect, at least a portion of the promoter is covalently bound to at least a portion of the ion exchange resin. In still another aspect, all or substantially all of the promoter is at least covalently bound to the ion exchange resin. In yet another aspect, the degree of attachment or binding between a promoter and an ion exchange resin can vary, such as, for example, covalent binding, ionic binding, and/or other interactions or attraction forces, and the present invention is not intended to be limited to any particular degree of attachment.

It should be noted that the methods described herein comprise multiple optional steps, and that no specific or required order of steps is intended, except where such an order would not be functional. One of skill in the art could readily determine which optional steps to utilize and in which order any reaction steps should be performed so as to produce a desired result.

Condensation Reaction

In one aspect, the reactants, phenol or optionally purified phenol, and at least one of a ketone or aldehyde, can be fed into a reactor vessel and contacted. In another aspect, the reactants, once in a reactor vessel, can be mixed using, for example, a static mixer. After contacting and/or mixing, the reactor feed comprising the reactants can be cooled to a predetermined temperature using, for example, a plate heat exchanger. In one aspect, use of the attached promoter catalyst system can allow for a reduction in the amount of acetone in the reactor feed stream, for example, from about 9.5 wt. % to about 5 wt. %. In such an aspect, the reactor effluent can have a lower solids content and a higher quantity of phenol.

A bed of the attached promoter ion exchange resin catalyst system, such as, for example, a cross-linked ion exchange resin catalyst with attached dimethyl thiazolidine promoter) can be disposed in the reaction vessel, such that the reactants flow through the bed. In one aspect, the reaction vessel and bed can be oriented such that the reactants flow downward (e.g., gravity-fed) through the catalyst bed.

In various aspects, the reaction can be controlled to a predetermined temperature, for example, about 55° C. or 65° C. Variations in temperature can affect the rate of reaction and rate of isomerization of any produced BPA. Other temperatures not recited herein can be utilized, and one of skill in the art could readily determine an appropriate temperature at which to conduct a particular condensation reaction.

In one aspect, the reactor can be capable of converting at least about 90% of the acetone, if present, in the reactor feed. In other aspects, the reactor can be capable of converting at least about 92%, 94%, 96%, 98%, or more of the acetone, if present, in the reactor feed. In another aspect, the reactor and attached promoter catalyst system can be capable of producing the p,p-BPA isomer with a selectivity of at least about 90%. In other aspects, the reactor and attached promoter catalyst system can be capable of producing the p,p-BPA isomer with a selectivity of at least about 90%, at least about 92%, at least about 93%, at least about 95%, at least about 97%, or more.

Once passed through the catalyst bed, the reactor effluent can optionally be subjected to a separate ion exchange resin bed to remove any undesired materials, such as, for example, oligomers, from the process stream. In one aspect, the reactor effluent is subjected to a separate ion exchange resin bed to remove any undesired materials. In another aspect, the reactor effluent is not subjected to a separate ion exchange resin bed.

Water Removal

After reaction, the effluent stream can optionally be subjected to a water removal step to remove residual water. In various aspects, a water removal step, if performed, can comprise one or multiple columns positioned in sequence.

In one aspect, the reactor effluent stream can comprise water, acetone, phenol, toluene and/or other aromatic solvents, such as, for example benzene and xylene. In one aspect, the effluent (i.e., vapor) can be subjected to a water cooled process condenser. In another aspect, the vent gas from such process condenser can be conveyed to a brine vent condenser, cooled by, for example, chilled brine at a temperature of about 8° C. It should be noted that the specific parameters (e.g., temperature) described herein are intended to be exemplary and non-limiting, and that one of skill in the art, in possession of this disclosure, could readily determine appropriate experimental conditions for a given process setup.

In another aspect, an inert gas, such as, for example, nitrogen, can be introduced in the condenser units so as to at least partially prevent the condensation of an aromatic solvent, such as, for example, toluene, that can be present in the effluent stream.

After passing through a water removal step, the reactor effluent (i.e., dehydrated reactor effluent) can have water content of less than about 0.5 wt. %, less than about 0.4 wt. %, less than about 0.3 wt. %, less than about 0.2 wt. %, or less than about 0.1 wt. %. In one aspect, the dehydrated reactor effluent has a water content of less than about 0.2 wt. %. In another aspect, the dehydrated reactor effluent has a water content of about 0.1 wt. %.

Phenol Recovery

To accommodate the change in reactor effluent from the use of an attached promoter ion exchange resin catalyst system, the reactor effluent stream, after optionally passing through a separate ion exchange resin bed and/or water removal step, can, in one aspect, comprise a phenol flash (i.e., phenol recovery) unit.

In various aspects, a phenol flash unit can comprise a single column or a plurality of individual columns. In various aspects, any combination of columns or order of columns can be utilized. In one aspect, a phenol flash unit comprises three individual columns: a phenol flash column, an upper phenol column, and a lower phenol column. In another aspect, any one or multiple columns can be removed from a process. It should be noted that the terms "upper" and "lower" are not intended to require a particular orientation, and the respective columns can be positioned in any geometric arrangement appropriate for a particular process.

In one aspect, the phenol flash column removes all or a portion of phenol reactants from the effluent stream. In a specific aspect, the reactor effluent, such as, for example, the dehydrated reactor effluent, can be heated prior to entering the phenol flash column. In another aspect, the phenol flash column can be operated at an elevated temperature and/or under vacuum, such as for example, about 750 mbar.

In one aspect, flashed phenol can be condensed after removal from the effluent stream. In another aspect, flashed phenol can be at least partially condensed using the feed stream to the flash column as a cooling medium. In such an aspect, at least a portion of the energy expended to flash the phenol can be recovered. Any remaining phenol vapors, if present, can be recovered by, for example, a vacuum system.

In one aspect, the effluent stream can be first subjected to a phenol flash column. The effluent from the phenol flash column can then be subjected to an upper phenol column, if present, and then to a lower phenol column.

In one aspect, the effluent from the phenol flash unit, for example, after passing through a phenol flash column, an upper phenol column, and a lower phenol column, can have a free phenol content of less than about 1.0 wt. %, less than about 0.75 wt. %, or less than about 0.5 wt. %. In a specific aspect, the effluent from the phenol flash unit has a free phenol content of less than about 0.5 wt. %.

It should be noted that, at any point in the process, an effluent stream can optionally be redirected back through one or more units and/or columns of the reaction process so as to further react and/or purify the effluent. One of skill in the art, in possession of this disclosure, could readily determine when any such recirculation loop should be employed so as to produce a desired product.

Solvent Crystallization

In one aspect, the reactor effluent, after being subjected to the phenol flash unit, can be fed to a solvent crystallization unit. In one aspect, a solvent crystallization unit can be used to remove BPA byproducts, such as, for example, o,p-BPA, chromans, BPX 1 and/or 2, CD1 and/or 2, LD2 and/or 2, or a combination thereof. In one aspect, the solvent crystallization unit can remove at least a portion of the BPA byproducts from the effluent stream. In one aspect, the solubility of one or more individual components in an effluent stream can be known or determined. In another aspect, such solubility data can be used by one of skill in the art to optimize the crystallization parameters so as to provide an improved product.

Properties of Produced Bisphenol-A

Reaction products of the various methods of the present invention can, in various aspects, exhibit higher purity levels than are attainable using conventional manufacturing processes. In one aspect, the use of an attached promoter ion exchange resin catalyst system, such as, for example, a dimethyl thiazolidine catalyst system, can provide a resulting BPA product that has no or substantially no inorganic or sulfur impurities. Moreover, the combination of an attached promoter catalyst system and a solvent crystallization step can provide products having high purity levels and that are suitable for use in the manufacture of food contact grade materials. For example, BPA produced using the methods of the present invention can be utilized in the manufacture of food-grade polycarbonate products.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Methods

In a first example, phenol and acetone are each fed to a reactor, where they are subsequently mixed using a static mixer. The reactor feeds are cooled using a plate heat exchanger before reaching the reactor vessel. A bed of ion exchange resin having an attached promoter (2% cross-linked ion exchange resin catalyst with DMT attached promoter) is disposed in the reactor such that the reactor feeds flow through the reactor in a downward fashion. Conversion of acetone in the reactor is designed to be at least about 90%, with a p,p-BPA selective of at least about 93%.

After reacting, the effluent stream is transferred to a separate vessel, where it passes through a bed of anion exchange resin to remove any free oligomer. The effluent is then subjected to a water removal step. After the water removal step, the dehydrated effluent stream is subjected to a phenol recovery step where a phenol flash column is used to remove phenol remaining in the effluent stream. The solvent crystallization unit can remove all or substantially all of the BPA byproducts. The remaining effluent stream can then be treated in a solvent recovery system to remove the aromatic solvent(s), such as toluene. The toluene or other aromatic solvent is thus separated from the BPA isomer stream.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. Listing A process for a chemical condensation reaction comprising contacting at least two chemical reagents comprising at least one of a phenol and a ketone with an attached promoter ion exchange resin catalyst system to produce an effluent stream, and then subjecting the effluent stream to a solvent crystallization step, wherein the attached promoter is an ion exchange resin catalyst system that comprises a cross-linked, sulfonated ion exchange resin having sulfonic groups, wherein the solvent used in the crystallization step comprises an aromatic solvent that comprises one or more of toluene, benzene, and xylene, and wherein the solvent crystallization step removes at least a portion of one or more bisphenol-A byproducts.

2. The process of claim 1, wherein the attached promoter ion exchange resin catalyst system has a degree of cross-linking of from about 1% to about 4%.

3. The process of claim 2, wherein the degree of cross-linking is from about 1.5% to about 2.5%.

4. The process of claim 2, wherein the degree of cross-linking is about 2%.

5. The process of claim 1, wherein the attached promoter ion exchange resin catalyst system comprises a dimethyl thiazolidine promoter.

6. The process of claim 1, wherein the attached promoter ion exchange resin catalyst system comprises a pyridyl ethylmercapton promoter.

7. The process of claim 2, wherein the attached promoter ion exchange resin catalyst system comprises a promoter that is ionically bound to from about 18% to about 25% of sulfonic acid groups present on the ion exchange resin.

8. The process of claim 2, wherein the attached promoter ion exchange resin catalyst system comprises a promoter that is ionically bound to from about 20% to about 24% of sulfonic acid groups present on the ion exchange resin.

9. The process of claim 1, wherein the sulfonated ion exchange resin is a sulfonated polystyrene ion exchange resin.

10. The process of claim 1, wherein the process does not comprise a bulk promoter.

11. The process of claim 1, wherein prior to the solvent crystallization step, a reactor effluent is subjected to at least one of a separate ion exchange resin bed, a water removal step, a phenol recovery step, or a combination thereof.

12. The process of claim 1, wherein the phenol comprises an aromatic hydroxy compound having at least one unsubstituted position.

13. The process of claim 1, wherein the reaction has a p,p-bisphenol A selectivity of at least about 90%.

14. The process of claim 1, wherein the effluent stream has a water content of less than about 0.5 wt %.

15. The process of claim 1, wherein the sulfonated ion exchange resin is cross-linked with polycyclic aromatic divinyl monomers, divinyl benzene, divinyl toluene, divinyl biphenyl monomers, or a combination thereof.

16. The process of claim 1, wherein the ion exchange resin is cross-linked with divinyl benzene.

17. A process to produce a bis-phenol A isomer comprising:
a) contacting at least two chemical reagents comprising at least one of a phenol and at least one of a ketone, an aldehyde, or a combination thereof, to produce a reactant feed;
b) contacting the reactant feed with an attached promoter ion exchange resin catalyst system to produce an effluent stream, wherein the attached promoter ion exchange resin catalyst system comprises a cross-linked, sulfonated ion exchange resin having sulfonic groups, and wherein the effluent stream comprises a bisphenol A isomer and an aromatic solvent that comprises one or more of toluene, benzene, and xylene;
c) passing the effluent stream through a phenol flash unit to remove a phenol reactant from the effluent stream; and
d) subjecting the effluent stream to a solvent crystallization step.

18. The process of claim 17, wherein the attached promoter ion exchange resin catalyst system comprises polystyrene, polysiloxane, or derivatives thereof.

19. The process of claim 17, wherein the sulfonated ion exchange resin is cross-linked with polycyclic aromatic divinyl monomers, divinyl benzene, divinyl toluene, divinyl biphenyl monomers, or a combination thereof.

20. The process of claim 17, wherein the sulfonated ion exchange resin is cross-linked with divinyl benzene.

21. The process of claim 17, wherein the attached promoter ion exchange resin catalyst system comprises a dimethyl thiazolidine promoter.

22. The process of claim 17, wherein the bisphenol-A isomer comprises p,p-bisphenol isomer.

23. A process for a chemical condensation reaction comprising contacting at least two chemical reagents comprising at least one of a phenol and a ketone with an attached promoter ion exchange resin catalyst system to produce an effluent stream, and then subjecting the effluent stream to a solvent crystallization step, wherein the attached promoter ion exchange resin catalyst system comprises a cross-linked, sulfonated ion exchange resin having sulfonic groups, wherein the degree of cross-linking is from about 1.5% to less than 2.0%, and wherein the solvent used in the crystallization step comprises an aromatic solvent comprising one or more of toluene, benzene and xylene.

24. The process of claim 23, wherein the attached promoter ion exchange resin catalyst system comprises a dimethyl thiazolidine promoter.

25. The process of claim 23, wherein the attached promoter ion exchange resin catalyst system comprises a pyridyl ethylmercapton promoter.

26. The process of claim 23, wherein the attached promoter ion exchange resin catalyst system comprises a promoter that is ionically bound to from about 18% to about 25% of sulfonic acid groups present on the ion exchange resin.

27. The process of claim 23, wherein the attached promoter ion exchange resin catalyst system comprises a promoter that is ionically bound to from about 20% to about 24% of sulfonic acid groups present on the ion exchange resin.

28. The process of claim 23, wherein the sulfonated ion exchange resin is a sulfonated polystyrene ion exchange resin.

29. The process of claim 23, wherein prior to the solvent crystallization step, a reactor effluent is subjected to at least one of a separate ion exchange resin bed, a water removal step, a phenol recovery step, or a combination thereof.

30. The process of claim 23, wherein the solvent crystallization step removes at least a portion of one or more bisphenol-A byproducts.

31. The process of claim 23, wherein the phenol comprises an aromatic hydroxy compound having at least one unsubstituted position.

32. The process of claim 23, wherein the reaction has a p,p-bisphenol A selectivity of at least about 90%.

33. The process of claim 23, wherein the effluent stream has a water content of less than about 0.5 wt %.

34. The process of claim 23, wherein the sulfonated ion exchange resin is cross-linked with polycyclic aromatic divinyl monomers, divinyl benzene, divinyl toluene, divinyl biphenyl monomers, or a combination thereof.

35. The process of claim 23, wherein the ion exchange resin is cross-linked with divinyl benzene.

* * * * *